(12) United States Patent
Semet

(10) Patent No.: US 7,101,376 B2
(45) Date of Patent: Sep. 5, 2006

(54) INTERLOCKING IM NAILS WITH THREADED GUIDEWIRE

(76) Inventor: Elliot Charles Semet, 403 Osprey Pt. Dr., Brielle, NJ (US) 08730

( * ) Notice: Subject to any disclaimer, the term of this patent is extended or adjusted under 35 U.S.C. 154(b) by 0 days.

(21) Appl. No.: 10/816,675

(22) Filed: Apr. 2, 2004

(65) Prior Publication Data

US 2005/0075635 A1    Apr. 7, 2005

Related U.S. Application Data

(60) Provisional application No. 60/459,953, filed on Apr. 4, 2003.

(51) Int. Cl.
*A61B 17/56* (2006.01)
(52) U.S. Cl. .................................... 606/72
(58) Field of Classification Search ............ 606/60, 606/62, 64–67, 72–74, 80, 86, 96, 103–104
See application file for complete search history.

(56) References Cited

U.S. PATENT DOCUMENTS

| | | | | |
|---|---|---|---|---|
| 2,049,361 A | * | 7/1936 | Ericsson | 606/103 |
| 2,821,979 A | * | 2/1958 | Cameron | 606/64 |
| 3,744,488 A | * | 7/1973 | Cox | 606/64 |
| 4,409,974 A | * | 10/1983 | Freedland | 606/60 |
| 5,034,012 A | * | 7/1991 | Frigg | 606/62 |
| 5,100,404 A | * | 3/1992 | Hayes | 606/62 |
| 5,472,444 A | * | 12/1995 | Huebner et al. | 606/64 |
| 5,743,908 A | * | 4/1998 | Kim | 606/64 |
| 5,770,705 A | * | 6/1998 | Shanbrom | 530/421 |
| 5,935,127 A | * | 8/1999 | Border | 606/62 |
| 6,224,600 B1 | * | 5/2001 | Protogirou | 606/63 |
| 6,231,576 B1 | * | 5/2001 | Frigg et al. | 606/62 |
| 6,551,321 B1 | * | 4/2003 | Burkinshaw et al. | 606/62 |
| 6,592,587 B1 | * | 7/2003 | Roger | 606/73 |
| 2002/0151898 A1 | * | 10/2002 | Sohngen et al. | 606/62 |

* cited by examiner

*Primary Examiner*—Eduardo C. Robert
*Assistant Examiner*—Annette Reimers
(74) *Attorney, Agent, or Firm*—Arthur M. Peslak

(57) ABSTRACT

A new method for locking Intramedullary Nails (IM Nails) with Threaded Guidewire. The present invention is practiced in conjunction with specifically designed tapered screws with segmented threads. This new design uses the screws to begin locking the IM Nail, followed by a threaded guidewire that is placed between screws of the IM Nail. Whenever a more proximal screw is placed with the threaded guidewire, it causes the guidewire to push/lock onto or around the distal screw eliminating the play and causing a more stable form of fixation.

6 Claims, 4 Drawing Sheets

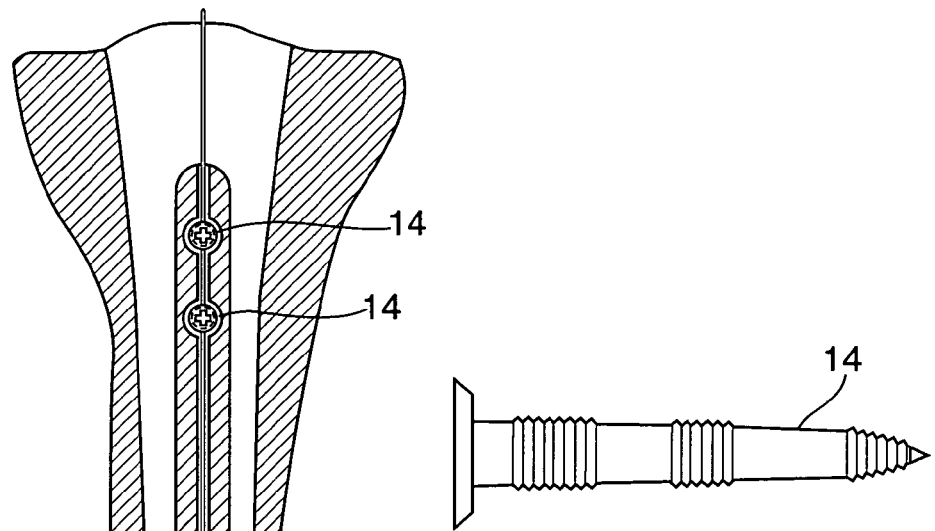
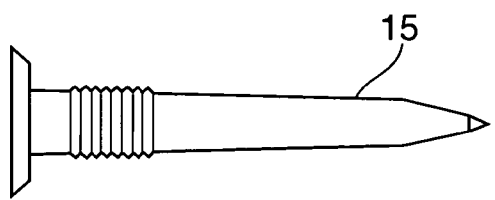
FIG. 5a
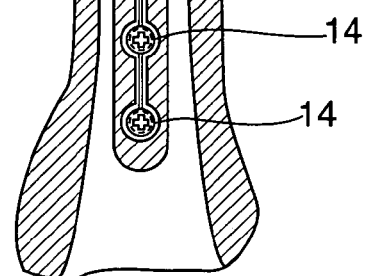
FIG. 5b
FIG. 3

INTERLOCKING IM NAILS WITH THREADED GUIDEWIRE

CROSS REFERENCE TO RELATED APPLICATIONS

Provisional Patent Application No. 60/459,953 with a filing date of Apr. 4, 2003.

BACKGROUND OF THE INVENTION

The present invention is directed to the field of orthopedic surgery. In particular, the present invention is directed to a new method for fracture reduction.

The currently available methods of fracture reduction are:
Casts/Braces
Plates:
Conventional
  Locking
External Fixation
Intramedullary Nails Intramedullary nails have several advantages over other forms of fixation:
  They are less invasive than plates;
  They have a lower infection rate;
  Nails are stronger than plates;
  Nails have a mechanical advantage compared to plates;
  The screws used with nails are more resistant to breakage due to the decreased moment arm;
  Nails have a high rate of union;
  Nails allow for anatomic alignment;
  Casts/braces immobilize the limb and do not allow early motion; and
  External fixators have a risk of pin tract infections.

One of the currently available methods of interlocking IM Nails is to solely use screws, which can result in loss of reduction because of the inherent play in the screw-nail interface. A second method of interlocking IM Nails is to cap the screw at the contra lateral cortex, which increases fixation in the cortical bone. However, this method does not help the screw-nail interface, Additionally, pressure applied by the capping on one end may cause the distal end to move out of position. A third available method of interlocking IM Nails is to have the hole of the IM Nail lined with rubber to provide a more grippable material for the screws. However the inherent play in rubber does not provide sufficient locking. The rubber-lined IM Nails also suffer from the disadvantage of the possibility for foreign body reactions if flaking of the rubber occurs.

The method of the present invention, with a threaded guidewire in between the screws, locks the screw in place, eliminates play, and results in a more stable form of fixation of a fracture.

Two other patented methods of interlocking IM Nails were found, however, neither are currently marketed:
  An interlocking Intramedullary Nail (U.S. Pat. No. 6,524, 314, granted Feb. 25, 2003) provides for a different mechanism, using 2 lag screws and a locking screw. This product is currently not marketed but would be a difficult mechanism because there are only a couple of safe zones where the screws can be placed. With the addition of two screws placed for fixation, it may be difficult to find safe zones. Additionally, the screws may cross thread early prohibiting further insertion.
  An interlocking Intramedullary Nail U.S. Pat. No. 6,019, 761, granted Feb. 1, 2000) provides for interlocking by placing a guidewire through one screw hole up to and out of the next. This patent also relies on drilling holes versus already manufactured holes and dropping wires through the holes and using the screws to cause the wires to interlock to the screws. This patent has a completely different means by which the interlocking would occur and be enhanced.

BRIEF DESCRIPTION OF THE DRAWINGS

FIG. 3 is a sectional view illustrating the present invention with screws attached to the guidewire.

FIGS. 5a and 5b illustrate an alternate embodiment of screws used in the present invention.

BRIEF SUMMARY OF THE INVENTION

The present invention provides for a new method for locking Intramedullary Nails (IM Nails) with a Threaded Guidewire. The current methods of interlocking screws results in inherent play in the screw-nail interface and therefore can result in loss of reduction. The present invention uses screws to begin locking the IM Nail, followed by using a threaded guidewire that is placed between screws of the IM Nail. By placing a more proximal screw with the threaded guidewire, the guidewire is pushed/locked onto or around the distal screw eliminating the play and causing a more stable form of fixation.

The screws of the present invention may be tapered and partially, segmented or fully threaded. The tapering and threading allows for maximum screw strength, a lag effect, centering of the IM Nail and fixation to the nail.

A new method of locking Intramedullary Nails is to use threaded guidewire. The threaded guidewire is placed in between screws of an intramedullary nail. Whenever a more proximal screw is placed with the guidewire, the more distal screw is locked to the nail. In addition, movement or play of the more proximal screw is minimized. This new design, including both the guidewire and screw, locks the screw in place to eliminate this play and result in a more stable form of fixation.

DETAILED DESCRIPTION OF THE PRESENT INVENTION

Figure 1:
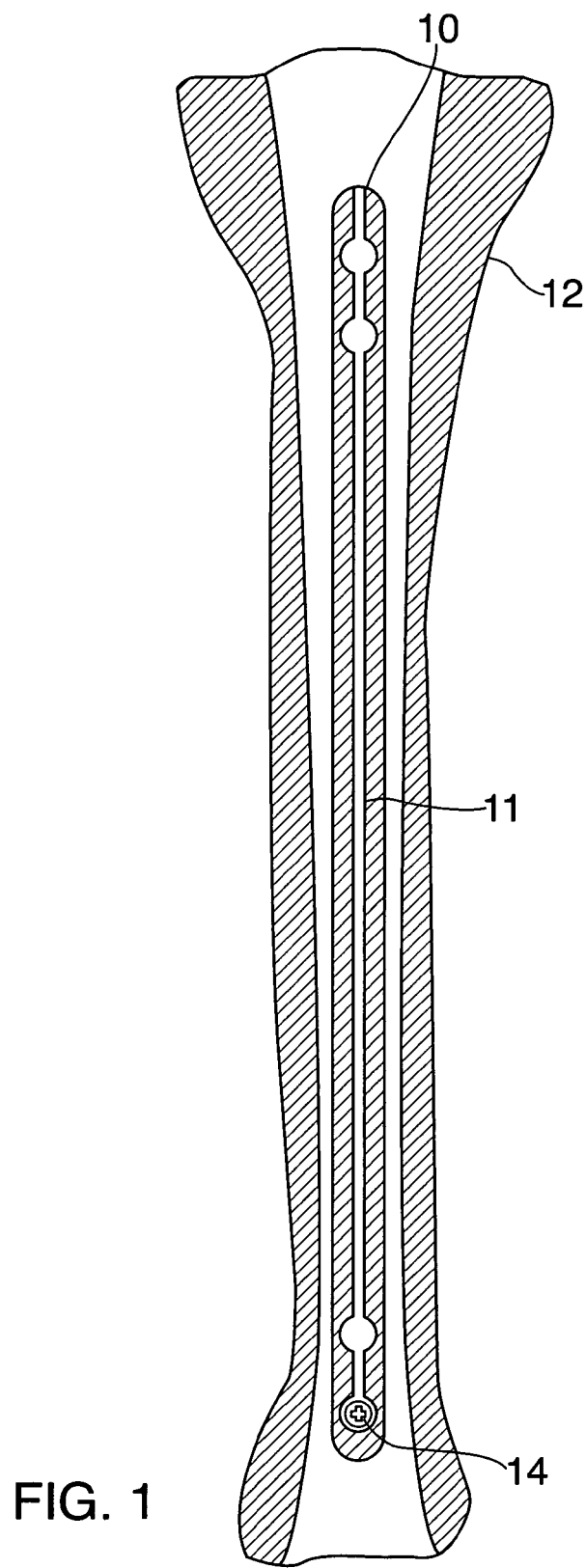
FIG. 1 is a sectional view of a bone illustrating the use of the method of the present invention.
Figure 2:
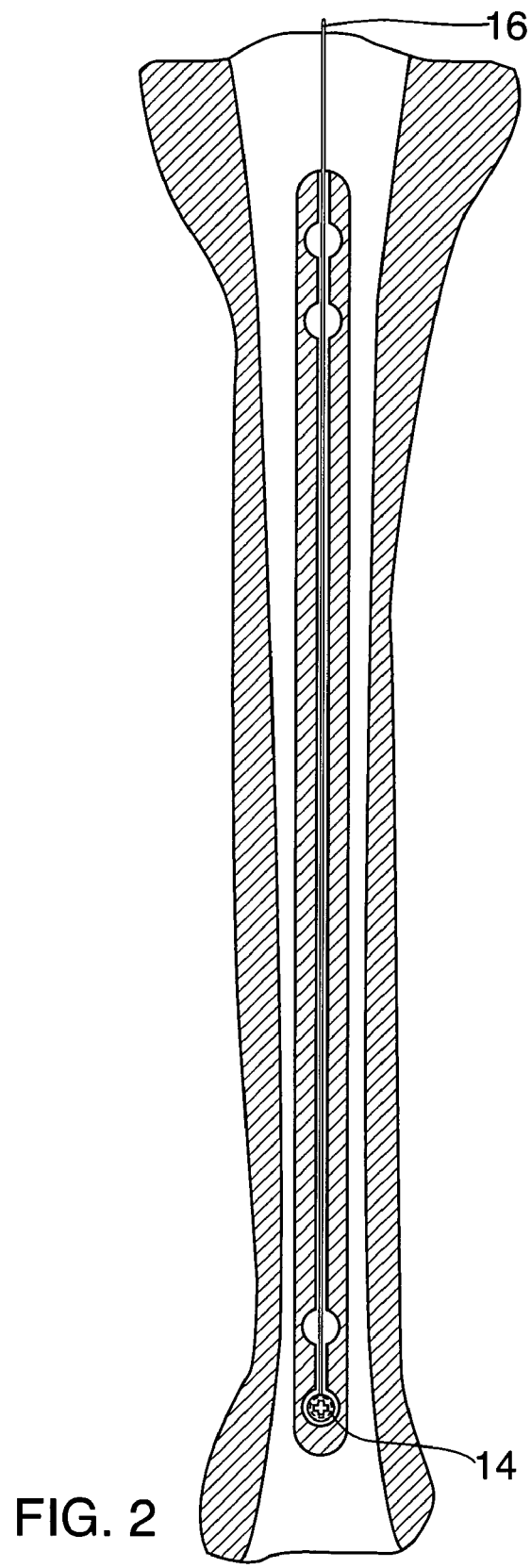
FIG. 2 is a section view illustrating the present invention with a guidewire inserted.
Figure 4:
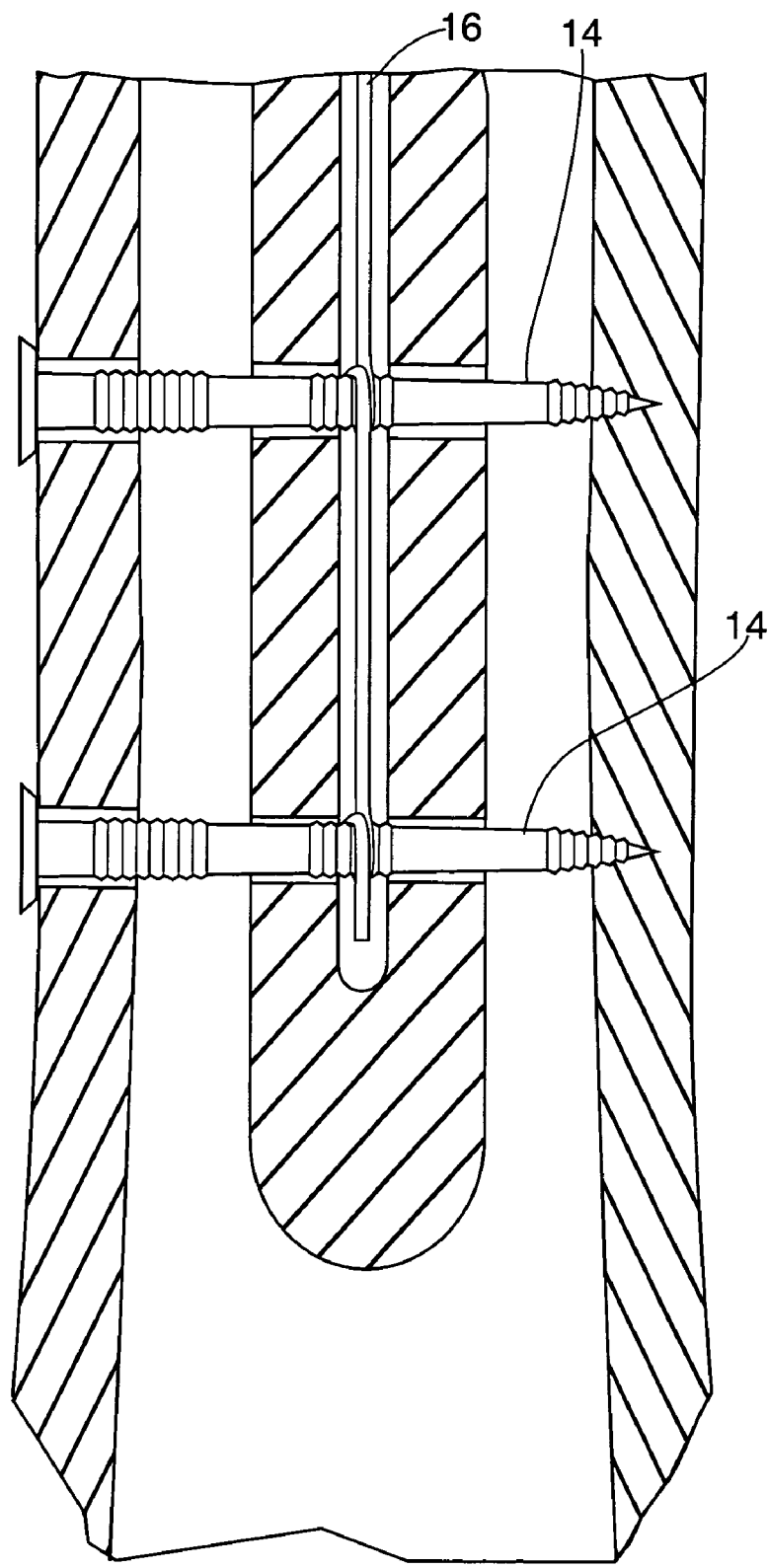
FIG. 4 is a detailed sectional view.

An Intramedullary Nail 10 ("IM Nail") is inserted into the cortical bone 12. The IM Nail is secured therein by a plurality of screws 14 and a threaded guidewire 16. This method will secure and eliminate relative movement of the screws 14 and the IM Nail 10. The IM Nail 10 comprises a guidewire track 11 through the inside that connects each of the screw openings. As shown in FIG. 1, the first most distal of the plurality of screws 14 is inserted and locked to the IM Nail 10. A threaded guidewire 16 is then inserted through the guidewire track 11 of the IM Nail 10. The more proximal screw 14 will exert a force that pushes the threaded guidewire 16 into the more distal screw 14 and causes the guidewire 16 and distal screw threads 14 to interlock. The exerted force of the more proximal screw 14 is caused by the length of the threaded guidewire 16. When the proximal screw 14 is tightened, it pushes the guidewire 16 down further to the distal screw 14 causing a secure or interlocking connection. The distal screw 14 may or may not be further secured by tightening/turning of the proximal screw 14 such that it further pulls the guidewire around the distal screw aiding in locking.

The interlocking occurs due to the pressure of the guidewire 16, the wrapping of the guidewire around one or both of the screws 14, through perforations within the screw 14, or other means that results in interlocking. There may be other alternative means of pushing the threaded guidewire 16 into or around the more distal screw 14 and causing interlocking. However, direct manual pressure applied on the guidewire 16 may cause the guidewire 16 to break as the proximal screw 14 is inserted. An alternative mechanism may be utilized to push the threaded guidewire 16 into the more distal of the plurality of screws 14 and cause them to interlock. Additionally, the guidewire 16 may be curved on the bottom or have a "Y" shape in order to aid locking around the most distal of the plurality of screws 14.

The plurality of screws 14 may also be designed such as to be tapered and segmented, partial or full threading. The tapering would ensure the initial threads on the tip pass through the guidewire 16 without early gripping. The middle threads would engage the guidewire 16 and the IM Nail 10. The wider end of the screw 14 would eliminate movement of one end of the screw 14, while the other end will rely on the guidewire 16 to eliminate play. An alternate embodiments screw, 15, is presented in FIG. 5*b*.

The method described above is then repeated for additional screw sets so that the most proximal screw will always lock in the previous screw placed in. The final-screw can be locked with an end cap that has a threaded tip that can exert more pressure on the most proximal screw. This method can be used in conjunction with other locking mechanisms.

What is claimed is:

1. A method for reducing fractures comprising the steps of:
   (a) Inserting an intramedullary nail into a cortical bone of a patient wherein the intramedullary nail comprises a hollow interior for use as a guidewire track and a plurality of screw openings adapted to receive a plurality of screws;
   (b) Inserting a first distal screw and locking the first distal screw in a first screw opening;
   (c) Inserting a threaded guidewire through the guidewire track;
   (d) Inserting a second screw proximal to the first distal screw and tightening the second screw thereby pushing the threaded guidewire into the first distal screw and causing the guidewire and first distal screw threads to interact; and
   (e) Inserting sequentially each of the remainder of the plurality of screws and tightening each of the remainder of the plurality of screws thereby pushing the threaded guidewire into a previously inserted screw and causing the guidewire and threads on the previously inserted screw to interact so that the plurality of screws necessary to reduce the fracture are inserted and tightened in place.

2. The method of claim 1 wherein the plurality of screws are perforated as a means to accept the threaded guidewire.

3. The method of claim 1 wherein the plurality of screws are tapered with partial threading as a means to accept the threaded guidewire.

4. The method of claim 1 wherein the plurality of screws are tapered with segmented threading as a means to accept the threaded guidewire.

5. The method of claim 1 wherein the plurality of screws are tapered with full threading as a means to accept the threaded guidewire.

6. The method of claim 1 wherein the guidewire has a "Y" shaped bottom to aid in locking the most distal screw.

* * * * *